United States Patent [19]

Anderson et al.

[11] Patent Number: 5,262,524
[45] Date of Patent: Nov. 16, 1993

[54] METHOD FOR THE SYNTHESIS OF TRIFUNCTIONAL MALEIMIDE-ANTIBODY COMPLEX

[75] Inventors: Leslie D. Anderson, Encinitas; Clarence N. Ahlem, San Diego; Ann E. Huang, Carlsbad, all of Calif.

[73] Assignee: Hybritech Incorporated, San Diego, Calif.

[21] Appl. No.: 793,051

[22] Filed: Nov. 15, 1991

Related U.S. Application Data

[62] Division of Ser. No. 491,386, Mar. 9, 1990, Pat. No. 5,091,542.

[51] Int. Cl.$^5$ .................. A61K 35/14; A61K 39/00; C07K 3/00; C12Q 1/00
[52] U.S. Cl. .................. 530/391.1; 530/387.3; 435/7.1; 424/85.8; 548/521
[58] Field of Search .................. 435/2, 4, 6, 7.1; 424/85.8; 530/387, 388, 389; 548/521

[56] References Cited

U.S. PATENT DOCUMENTS 5,091,542  2/1992  Ahlem et al. .................. 548/521

FOREIGN PATENT DOCUMENTS

| | | |
|---|---|---|
| 0178125 | 10/1985 | European Pat. Off. . |
| 0417188 | 5/1989 | European Pat. Off. . |
| 2018253 | 4/1979 | United Kingdom . |

*Primary Examiner*—Robert J. Hill, Jr.
*Assistant Examiner*—Gian P. Wang
*Attorney, Agent, or Firm*—Paul C. Steinhardt; June M. Bostich; Donald J. Pochopien

[57] ABSTRACT

The present invention is directed to a method for extending the length of one of the three linker arms of the compound of Formula I in the production of novel trifunctional antibody-like compounds. Formula I is defined as follows:

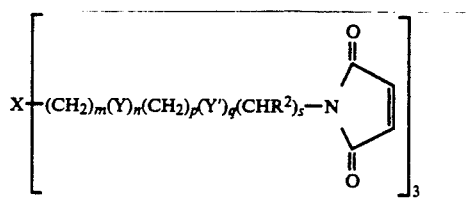

wherein X is

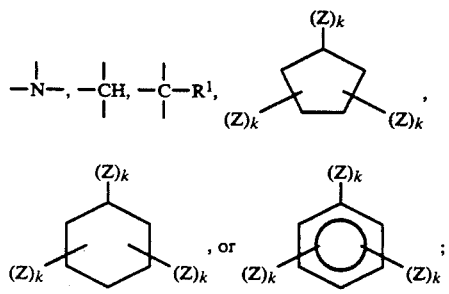

wherein k = 1 or 0;
wherein Z is

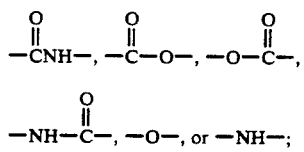

wherein s = 1 or 0;
wherein n = 1 or 0;
wherein q = 1 or 0;
wherein Y is

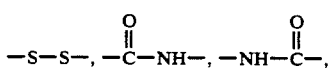

(Abstract continued on next page.)

ABSTRACT
-continued

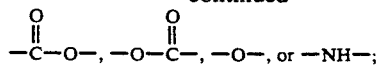

wherein Y' is

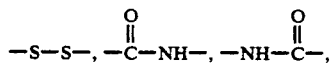

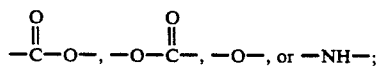

wherein p or m may be the same or different and are integers ranging from 0 to 20 with the provisos that when n=0, the sum of m and p is an integer ranging from 1 to 20, whereas when n=1, p and m are each an integer that is at least 1 and the sum of p and m is an integer ranging from 2 to 20;

wherein $R^1$ is straight or branched chain lower alkyl having from 1 to 6 carbon atoms or lower alkoxy having from 1-6 carbon atoms; and wherein $R^2$ is hydrogen, phenyl, —COOH, or straight or branched chain lower alkyl having from 1-6 carbon atoms, with the proviso that the lower alkyl moiety may be mono substituted by —$NH_2$, —OH, or —COOH.

The compound of the present invention is useful as a trivalent coupling agent for linking Fab'-like fragments to form both bifunctional and trifunctional antibody-like compounds.

9 Claims, No Drawings

METHOD FOR THE SYNTHESIS OF TRIFUNCTIONAL MALEIMIDE-ANTIBODY COMPLEX

This is a division, of application Ser. No. 491,386, filed Mar. 9, 1990, now U.S. Pat. No. 5,091,542.

BACKGROUND OF THE INVENTION

A. Field Of The Invention

The present invention is directed to a trivalent coupling agent. More particularly, the present invention is directed to a tris-maleimido compound having three linker arms of variable length, charge, lability and hydrophobicity. Such compounds are useful as intermediates in the synthesis of bifunctional and trifunctional (i.e., tri-specific) antibody-like compounds which are useful in medical diagnoses, therapeutics and diagnostic/therapeutic combinations.

B. Background

Antibodies are complex protein molecules generated by an organism's immune system in response to an antigen perceived by the host as being foreign. The extreme plasticity and diversity of an animal's immune repertoire permits the generation of an enormous variety of antibody molecules to an equally large number of antigens. However, individual antibodies are monospecific and therefore merely monofunctional for purposes of this invention.

Landsdorp, et al. teaches the formation of a bifunctional antibody complex formed by cross linking two monoclonal antibodies of different specificities but of the same isotype. Landsdorp, et al., "*Cyclic Tetramolecular Complexes Of Monoclonal Antibodies: A New Type Of Cross-linking Agent,*" *Eur. J. Immunol.*, 16, p. 679-83 (1986). Landsdorp's cross-linking agent consisted of two anti-isotype antibody molecules, which cross-linked the two monoclonal antibodies to form a cyclic tetramolecular complex that was bifunctional. Implicitly, the intact antibodies taught by Landsdorp have Fc regions which are capable of binding complement and/or stimulating an immune response if presented in vivo.

An object of the present invention is to avoid the use of antibodies or linkers having Fc regions which may bind, complement, and/or stimulate an immune response by the antibody-target complex.

Reading (U.S. Pat. No. 4,714,681) teaches the creation of bifunctional antibody-antibody chimeras by the fusion of two different hybridoma cell lines which produce monoclonal antibodies of different specificities (quadroma) and by the fusion of a hybridoma producing a specific monoclonal antibody with a lymphocyte producing a different antibody. The success of this method depends on the ability of the hybrid cells to produce both the heavy and light chains of both parental types in equal amounts such as to maximize the potential for the random assembly of heavy and light chains to yield the appropriate bifunctional complex. At best, this random assembly of antibody subunits can result in only one of eight molecules (12.5%) being of the desired specificities. Moreover, Reading's chimeras are whole antibodies that have intact Fc regions. Consequently, when injected into a "foreign" species, Reading's chimeras, like Langsdorp's bifunctionals, have the potential to invoke an interaction with components of the immune system that bear Fc receptors (e.g., macrophages, complement, etc.).

Among the first descriptions of the use of chemical compounds to covalently cross-link antibodies was Hamaguchi et al., *J. Biochem,* 85; 1289-1300 (1979). Hamaguchi describes the synthesis of a bifunctional-antibody-$\beta$-galactosidase compound which is cross-linked via N,N'-o-phenylenedimaleimide. Hamaguchi's compound was reported useful in sandwich enzyme immunoassays. Glennie et al., *J. Immunol.,* 139, 2367-2375 (1987), also describes the linking of two Fab' fragments utilizing the compound taught in Hamaguchi, i.e., o-phenylenedimaleimide.

Notwithstanding their characterization as bifunctional, when used as pharmaceutical agents, the bifunctional antibodies and bifunctional Fab' compounds of the prior art have the inherent limitation of being monofunctional at their site of action. This limitation arises because the first of the two specificities of the bifunctional molecule must be directed to the site of action, i.e., the organ, tissue or antigen of interest. This leaves only a single specificity for conferring mono-function to the molecule once it has become immobilized at its site of action. It is an object of the present invention to develop an intermediate compound, i.e., a multifunctional coupling agent, that is suited for producing a novel series of pharmaceutical agents capable of being trifunctional overall, and thus bifunctional at their site of action.

SUMMARY OF THE INVENTION

The present invention is directed to a compound for use as an intermediate in the production of trifunctional antibody-like molecules. The intermediate compound of the present invention functions as a trivalent agent that is capable of coupling two or three Fab'-like fragments. Specifically, the intermediate compound of the present invention is a trivalent coupling agent of the formula:

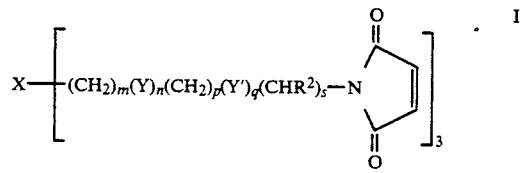

wherein X is

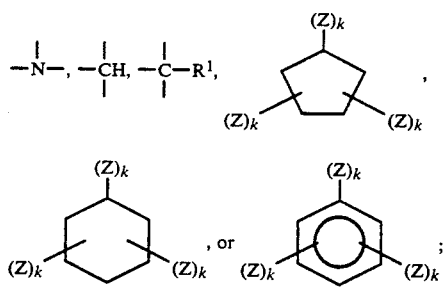

wherein k=1 or 0;
wherein Z is

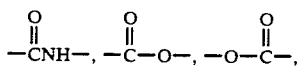

-continued

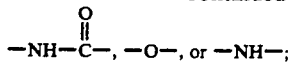

wherein s=1 or 0;
wherein n=1 or 0;
wherein q=1 or 0;
wherein Y is

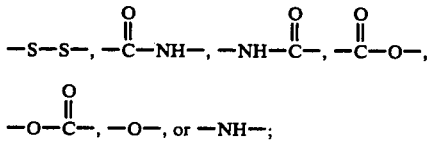

wherein Y' is

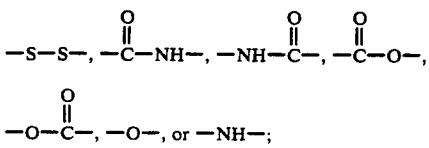

wherein p or m may be the same or different and are integers ranging from 0 to 20 with the provisos that when n=0, the sum of m and p is an integer ranging from 1 to 20, whereas when n=1, p and m are each an integer that is at least 1 and the sum of p and m is an integer ranging from 2 to 20;
wherein $R^1$ is straight or branched chain lower alkyl having from 1 to 6 carbon atoms or lower alkoxy having from 1-6 carbon atoms; and
wherein $R^2$ is hydrogen, phenyl, —COOH, or straight or branched chain lower alkyl having from 1-6 carbon atoms, with the proviso that the lower alkyl moiety may be mono-substituted by —NH$_2$, —OH, or —COOH.

DETAILED DESCRIPTION OF THE INVENTION

The present invention is directed to a compound of Formula I as previously described. This compound has utility as an intermediate i.e., a trivalent coupling agent, for use in the formation of bifunctional and trifunctional antibody-like compounds. By "bifunctional antibody-like compounds" as used herein is meant compounds having two Fab'-like fragments covalently bonded thereto, preferably having different specificities and wherein the Fab'-like fragments substantially retain the antigen-binding activity of the whole antibodies from which they are derived. By "trifunctional antibody-like compounds" as used herein is meant compounds having three Fab'-like fragments covalently bonded thereto, preferably having different specificities, wherein the Fab'-like fragments substantially retain the antigen-binding activity of the whole antibodies from which they are derived. The bifunctional and trifunctional antibody-like compounds are preferably used as in vivo pharmaceutical agents having diagnostic, therapeutic, or a combination of diagnostic/therapeutic applications.

Structurally, the intermediate compound of the present invention, (hereinafter the "trivalent coupling agent" of the present invention), which is represented by Formula I, has a central moiety "X" from which 3 linker arms extend. The central moiety "X" may be a single atom, such as carbon or nitrogen, or a cyclic molecule that is capable of extending three linker arms therefrom. Suitable cyclic molecules may be or contain a 5 or 6 membered ring that is aliphatic or may be or contain a 6 membered ring that is aromatic. Preferred cyclic compounds are aromatic 6 membered rings, such as phenyl. Preferred positioning of the linker arms on the aromatic ring are at the 1, 3, and 5 positions. However, as the linker arms become longer, the positioning of the arms on the aromatic ring becomes less critical since steric hinderance at the terminus of the linker arms, due to coupling to the first Fab'-like fragment, becomes less of a factor.

The linker arms on the trivalent coupling agent of the present invention may be straight or branched chain aliphatic and comprise from about 1-20 carbon atoms. In terms of Formula I, the arms are straight chain aliphatic when n=0, s=0, and m and p are each an integer that is at least 1 and the sum of p and m is an integer ranging from 2 to about 20. Alternatively, the linker arms may be substituted along the way to confer desirable properties to the linker arms. For example, one or more of the linker arms may contain one or more amides or ester linkages along the chain to confer improved solubility. The amide linkages may be provided in whole or in part by the various alpha amino acids.

Expressed in terms of Formula I, the presence of a solubility enhancing amide on each linker arm is reflected when in Formula I, n=1 and Y=—CONH— or —NH—CO—. Alternatively, the presence of a solubility enhancing amide on each linker arm occurs when Z of Formula I is —CONH— or —NH—CO—. Further, the presence of two solubility enhancing amide linkages per linker arm occurs when Y of Formula I is —CONH— or —NHCO— and when Z of Formula I is independently —CONH— or —NHCO—.

The use of amino acids, such as serine, lysine, glutamic acid and the like, which have polar substituents, introduces even greater polarity into the linker arms of the trivalent coupling agent of the present invention, thereby further enhancing its water solubility. The need for polar substituted amino acids increases as the hydrophobicity of the linker arms increases, such as with increasing aliphatic chain length.

Since stereochemistry is retained during the synthesis of the compounds of the present invention (Examples 4-6), specific stereochemistry is introduced into the linker arms by the use of D or L amino acids.

Analogous to the amide linkages just discussed, each linker arm of the compound of the present invention may contain from 1-2 ester linkages to enhance the overall solubility of the compound of the present invention. This situation is reflected when Y and/or Z of Formula I are independently —COO— or —OCO—. Further it is within the scope of the present invention to mix esters and amides in the same linker arms such as when Z is an amide and Y is an ester of vice versa.

Optionally, one or more of the linker arms may contain a disulfide (—S—S—) linkage. The disulfide linkage may be symmetrically introduced by incorporating a cystine residue on each linker arm. However, the use of cystine is not particularly preferred due to the necessity to utilize blocking reactions to prevent the incorporation of multiple residues (i.e., peptide formation). A more preferred method for the symmetrical incorporation of a disulfide linkage into each linker arm is to utilize a disulfide containing alpha and omega terminated diamine of the formula:

$$H_2N-(CH_2)_j-h-S-S-(CH_2)_h-NH_2$$

wherein "j" and "h" are independently integers from 2-18 with the proviso that the sum of "j" and "h" is not greater than 20. Alternatively, the structurally analogous alpha and omega terminated dithio is used. The use of these compounds is discussed in detail herein, particularly as they relate to the selective introduction of a —S—S— linkage in a single linker arm. Expressed in terms of Formula I, a disulfide linkage occurs when n=1 and Y=—S—S—.

At or near the distal terminus of each linker arm is a maleimide moiety for binding to a free sulfhydryl group (—SH) on an Fab'-like fragment. The maleimide moiety exhibits selective reactivity with these free sulfhydryl groups at pH 5-8, preferably pH 5-7. However, as the pH increases towards 8, the maleimide moiety begins to increasingly react with free amino groups, such as the ε-amino group of lysine. At pH>8, the selectivity for sulfhydryl begins to decrease. Further, the reaction between the maleimide moiety and the amines begin to increase, due to both the large number of amines and their increasing nucleophilicity. Because of the large number of lysine residues, and thus free amino groups, on any Fab'-like fragment, the coupling between a maleimide moiety and any one of the free amino groups at pHs greater than 8 occurs with decreased specificity and may not result in a single reproducible product. In contrast, free sulfhydryl groups on Fab'-like fragments occur at 1-3 specific locations and in the hinge region, unless chemically modified or genetically engineered to specifically occur elsewhere. Thus, at pH 5-8, preferably 5-7, the reaction between the maleimide moiety and the sulfhydryl groups, which are uniquely positioned, allow for regiospecific and substantially reproducible binding of maleimide moiety at the hinge region or other specifically added location. Regiospecific binding at or near the hinge region is important because it not only permits the coupling of Fab'-like fragments in a reproducible manner, but is also permits binding to occur away from the antigen binding portion of the Fab'-like fragment, which minimizes adverse effects upon the specificity and/or affinity of the antibody.

"Fab'-like fragments" containing free sulfhydryl groups are produced by the enzymatic cleavage of a whole antibody at its hinge region. Typically, enzymatic cleavage of an antibody at the hinge region is effected either by pepsin or papain. By definition in the art, pepsin cleavage of a whole antibody, such as IgG, results in one F(ab')₂ fragment and one Fc' fragment. By definition in the art, papain cleavage of a whole antibody under reducing conditions results in two Fab fragments and one Fc fragment. The F(ab')₂ fragment that is obtained from the pepsin cleavage may be reductively cleaved to yield two Fab' fragments. An Fab' fragment is structurally similar to an Fab fragment in that both fragments contain the intact antigen binding regions of the antibody precursor. However, the Fab' fragment differs from the Fab fragment in that the Fab' fragment is slightly larger having more heavy chain. Typically, the Fab' fragment differs further from the Fab fragment by also having one or more additional sulfhydryl groups on its heavy chain.

Depending upon the species that is the source of the antibody, the number of disulfide bridges between the two heavy chains at the hinge region may vary. As a result, the number of free sulfhydryl (—SH) groups on the Fab and Fab' fragments may also vary from species to species. For example, the pepsin cleavage and subsequent reduction of mouse $IgG_1$, $IgG_{2a}$ and $IgG_{2b}$ antibody produces mouse Fab' fragments that have three free —SH groups. In contrast, the pepsin cleavage and subsequent reduction of human $IgG_1$ antibody produces two Fab' fragments that each have only two free —SH groups. Further, the papain cleavage of the same human $IgG_1$ results in two Fab fragments, each having only a single free —SH group. See U.S. Pat. No. 4,659,839 (Nicolotti, et al.) at col. 4 describing this latter cleavage. Human $IgG_1$ is of interest because it is the predominant subclass of monoclonal antibodies used in the constant region of chimeric antibodies.

The trivalent coupling agent of the present invention couples to Fab' fragments having 1, 2, or 3 free sulfhydryl (—SH) groups. However, Fab' fragments having 2 free sulfhydryl groups are especially preferred.

For purposes of the present invention, we collectively define the term "Fab'-like fragments" as including not only those Fab and Fab' fragments that have from 1-3 free sulfhydryl groups on their heavy chain, whether by natural occurrence, chemical modification or genetic engineering, but also as including Fv fragments that have been genetically engineered to possess from 1-3 sulfhydryl groups on either their heavy or light chain or on a combination of both. The "Fv fragment," which is a fragment derived from either an antibody, an Fab' fragment or an Fab fragment, contains the variable ("v") region of the antibody, which region provides specificity for the antigen of interest. In order for a genetically engineered Fv, Fab, or Fab' fragment to be useful in the present invention, the sulfhydryl group(s), which are engineered into the fragment, must be positioned so as not to substantially interfere with antigen binding capacity of the Fv, Fab, or Fab' fragment respectively. The determination of the number of the free sulfhydryl groups in Fab' fragments is well known in the art. U.S. Pat. No. 4,659,839 (Nicolotti, et al.), which issued on Apr. 21, 1987, describes such a method using ³H-(N-ethylmaleimide) and is incorporated herein by reference.

Preferably, the tris-maleimide compound of the present invention is used to couple Fab'-like fragments that have two free sulfhydryl (—SH) groups. As already disclosed above, such Fab'-like fragments are obtained by the pepsin cleavage and subsequent reduction of human $IgG_1$. In addition, preferred Fab'-like fragments that have two free sulfhydryl groups at the hinge region are also obtainable from appropriate human, primate (e.g., chimp), and human-mouse chimeric antibodies. For example, chimeric antibodies having a human constant region yield, upon pepsin cleavage and subsequent reduction, Fab'-like fragments that have two sulfhydryl groups in the hinge region. This is because the human constant region inherently includes the hinge region as a segment within it. These chimeric Fab'-like fragments with human constant regions are preferred for use in humans over Fab'-like fragments from non-human sources because the human constant region substantially reduces the likelihood of invoking an immune response. This is of paramount importance when the Fab'-like fragment is intended to be parenterally administered to humans as a pharmaceutical agent.

The trivalent coupling agent of the present invention is suited for coupling two or three Fab'-like fragments, to produce an antibody-like compound for use in diagnostics, therapeutics and/or diagnostic/therapeutic combinations. By "diagnostics" as used herein is meant testing that is related to either the in vitro or the in vivo diagnosis of disease states or biological status (e.g., pregnancy, infertility, etc.) in mammals, preferably in humans. By "therapeutics" and "therapeutic/diagnostic combinations" as used herein is respectively meant the treatment or the diagnosis and treatment of disease states or biological status via the in vivo administration to mammals, preferably humans, of bifunctional or trifunctional antibody-like molecules that utilize the trivalent coupling agent of the present invention.

A particularly preferred utility of the coupling agent of the present invention is to couple two or three Fab'-like fragments having different specificities to produce a bi- or trifunctional antibody-like compound respectively. The bifunctional antibody-like compound, which has two different Fab'-like fragments can be used as an in vivo diagnostic or therapeutic agent. In this utility, the first Fab'-like fragments has specificity for the organ, tissue or oncologic antigen of interest, whereas, the second Fab'-like fragment, depending upon utility, has specificity either for a diagnostic imaging or dosimetric isotope complex (e.g., $^{111}$In-ethanolaminethioureabenzyl-EDTA) or for a therapeutic agent (e.g., a therapeutic radioisotope complex or an antigen coupled to a chemotherapeutic agent).

The trifunctional antibody-like compounds, which are also produced via the trivalent coupling agent of the present invention, have several utilities. These utilities include use as a diagnostic agent, therapeutic agent or as a combination diagnostic/therapeutic agent. A preferred utility is as a combination diagnostic/therapeutic agent. In this latter utility, the first Fab'-like fragment has specificity for an organ, tissue or oncologic antigen of interest and binds thereto. The second Fab'-like fragment has specificity for a diagnostic imaging or dosimetric/isotope complex (e.g., a chelated nuclide or paramagnetic agent) that permits the imaging of an organ or tissue of interest and/or the diagnosis of a condition (e.g., cancer) associated with that organ or tissue. The third Fab'-like fragment has specificity for a therapeutic agent that can optionally be administered to the patient should the expected condition present itself to a physician upon the imaging of the organ, tissue or cancer via the immobilized second Fab'-like fragment and its antigen. Thus, the trivalent coupling agent of the present invention enables the production of a trifunctional pharmaceutical composition that is bifunctional (i.e., both diagnostic and therapeutic) at the site of action.

Alternatively, in its utility as a pure diagnostic agent, the second and third Fab'-like fragments of the trifunctional antibody-like compound have specificity for the same or different diagnostic imaging or dosimetric complexes. Whereas, in its utility as a pure therapeutic agent, both the second and third Fab'-like fragments of the trifunctional antibody-like compound have specificity for the same or different therapeutic agents.

There are instances when a trifunctional antibody like compound ("TFA") having specificities for two different tumor antigens might be useful. There is some evidence that melanoma may express either the p96.5 or the gp240 antigen or both. If this is true, then a TFA with binding specificities directed toward these two antigens in conjunction with an anti-chemotherapeutic, anti/imaging, or anti/therapeutic isotope might be useful. A similar situation may exist in lung cancer, with some tumors expressing the KS1/4 antigen or CEA, or both. Thus, in its utility as either a diagnostic or as a therapeutic agent, the first and second Fab'-like fragments have specificities for the different antigens expressed on or by the same tumor or tissue.

An Fab'-like fragment can have specificity for a therapeutic agent either directly or indirectly. Specificity for a therapeutic agent is "direct" when the Fab' fragment is specific for the therapeutic agent itself. Specificity for a therapeutic agent is "indirect" when the Fab' fragment is specific for a select antigen or hapten to which the therapeutic agent is coupled. When an Fab'-like fragment has specificity for a select antigen or hapten, one can vary the number and type of therapeutic agent attached to the select antigen or hapten, thereby permitting the treating physician to vary the treatment depending upon factors such as the condition presented, the severity of the condition, the patient's sensitivity to particular pharmaceuticals, and the presented condition's response to certain pharmaceuticals. One could even co-administer two therapeutic agents bound to the same select antigen or hapten to provide a localized synergistic effect at the organ, tissue, or tumor of interest.

Examples of therapeutic agents capable of "directly" binding to an Fab'-like fragment include chelate complexes that are formed between chelating agents and chelatable radionuclides that are $\beta$-emitters. Suitable chelating agents for the radionuclides (and/or the paramagnetic metal ions used in diagnosis) are polyacidic organic molecules that further contain organic nitrogen, phosphorous, oxygen or sulfur. By way of example, suitable chelating agents include ethylenediaminetetraacetic acid ("EDTA"); ethanolaminethioureabenzyl-EDTA ("EOTUBE"); diethylenetriaminepentaacetic acid ("DTPA"); methylthioureabenzyl DTPA ("MeTUBO"); 1,4,7,10-tetrazacyclododecane-N',N",N''',N''''-tetraacetic acid ("DOTA"); L-aminobenzyl-EDTA, and the like. Other suitable organic chelating agents are disclosed in U.S. Pat. No. 4,647,447 (Gries et al.) which is incorporated herein by reference. Suitable $\beta$-emitters are the chelatable ions of $^{67}$Cu, $^{186}$Rh, $^{188}$Rh, $^{189}$Rh, $^{153}$Sm, $^{90}$Y, and $^{111}$In (Aüger).

Examples of therapeutic agents capable of becoming "indirectly" bound by an Fab'-like fragment are compounds of the formula:

Substrate-Cytotoxic Agent wherein the "substrate" has at least one epitope bindable by the Fab'-like fragment and is the substrate for an enzyme or an active fragment thereof, and wherein reaction of the enzyme with the bound Substrate-Cytotoxic Agent cause release of the cytotoxic agent from the substrate.

The term "Cytotoxic Agent" as used herein means compounds that are useful in the treatment of neoplasms, whether benign or malignant. Such drugs include, in general, alkylating agents, antiproliferative agents, tubulin-binding agents, cytotoxins in general, and the like. Preferred classes of such compounds are the nitrogen mustard agents, the vinca alkaloids, the daunomycin family, the mitomycins, the bleomycins, the cytotoxic nucleosides, the pteridine family of drugs, the podophyophyllotoxins, the sulfonylureas (as described in European Patent Publication No. 222,475, published May 20, 1987), and low molecular-weight toxins such as the trichothecenes and the colchicines. Particularly preferred members of those classes include, for example, doxorubicin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, etoposide, melphalan, vinblastine, vincristine, leurosidine, vindesine, leurosine, trichothecene, desacetylcolchicine, and the like.

The conversion of trivalent antibody-like compounds into diagnostic, therapeutic and combination diagnostic/therapeutic agents is discussed in more detail in our copending U.S. patent application Ser. No. 07/491,406, cofiled herewith.

As already pointed out, the trivalent coupling agent of the present invention is suited for coupling to Fab'-like fragments having one, two, or three, free sulfhydryl groups (—SH) i.e., sulfhydryl moieties. However, the number of trivalent coupling agents of the present invention that are required to form a trifunctional antibody-like compound will vary from 1-2 depending upon the number of free sulfhydryl groups on the Fab' fragments. For example, three Fab' fragments, each having a single free —SH group, require only one trivalent coupling agent of the present invention to accomplish coupling to produce a trifunctional antibody-like molecule. In contrast, three Fab'-like fragments (designated as $F_1ab', F_2ab', F_3ab'$), each having two free sulfhydryls, would usually require two trivalent coupling agents of the present invention to give rise to a trifunctional antibody-like compound. Likewise, three Fab'-like fragments each having three free sulfhydryl groups would require two trivalent coupling agents of the present invention. Moreover, two or three Fab'-like fragments with different numbers of free sulfhydryls could also be combined to produce a bifunctional or trifunctional antibody-like molecule respectively. However, it is most preferred to use trivalent coupling agents of the present invention to couple two or three Fab'-like fragment wherein each fragment has two free sulfhydryl groups.

Scheme I generically provides the reaction sequences for using the trivalent coupling agent, XI, of the present invention, wherein XI is a schematic representation of the compound of Formula I, to couple three Fab'-like fragments each having two free sulfhydryl groups. The trivalent coupling agent, XI, may be dissolved in a small volume (<10% of the reaction volume) of organic solvent to which is added the Fab'-like fragment to be derivatized. In Scheme I, a molar excess, preferably at least 10 fold, more preferably at least 20 fold, most preferably at least 30 fold, of XI is combined in an aqueous buffer at pH 5-8, preferably pH 5-7, with a first Fab'-like fragment, $F_1ab'$. In the ensuing reaction, two of the three terminal maleimides on the trivalent coupling agent, XI, react with the two free sulfhydryl groups (—SH) of the first Fab'-like fragment, $F_1ab'$, to produce a coupled product XII having only a single reactive maleimide moiety remaining. The proximity of the two sulfhydryl groups (—SH) on the Fab'-like fragment and the relative position of the linker arms on the coupling agent permits the second maleimide moiety of the coupling agent to instantaneously couple to the second sulfhydryl (—SH) group once the first coupling has taken place. The coupled product XII is then separated by gel filtration from excess XI whereupon XII is reacted in an aqueous buffer at pH 5-8, preferably pH 5-7, with a second Fab'-like fragment, designated $F_2ab'$ and having a second specificity. The resultant product XIV is a bifunctional Fab'-like moiety having a single free sulfhydryl group (—SH) for coupling with a second trivalent coupling agent of the present invention. In a separate reaction shown in Scheme I, a third Fab'-like fragment, $F_3ab'$, having a third specificity, is reacted as described above in aqueous solution at pH 5-8, preferably pH 5-7, with a molar excess of the trivalent coupling agent of the present invention, XV, which may be the same or different than XI. For example, unlike XI, XV may have labile linker arms that contain a disulfide linkage (—S—S—) within each of the arms. Alternatively, the linker arms of XV may vary from the linker arms of XI in length, polarity, or a variety of other factors to accommodate the Fab'-like fragment being coupled. As previously described for XI, the trivalent coupling agent, XV, may be dissolved in a small volume (<10% of the aqueous reaction volume) of organic solvent to which is added the Fab'-like fragment to be derivatized. In Scheme I, the coupling of $F_3ab'$ to XV produces a compound XVI having a single free maleimide moiety. The subsequent reaction of products XIV and XVI in aqueous solution at pH 5-8 produces a trifunctional antibody-like compound XVII that incorporates the trifunctional coupling agent of the present invention. The generic use of the trivalent coupling agent of the present invention to prepare trifunctional antibody-like compounds is more fully discussed in Example 12 herein. Specific uses are described in Examples 13 and 14.

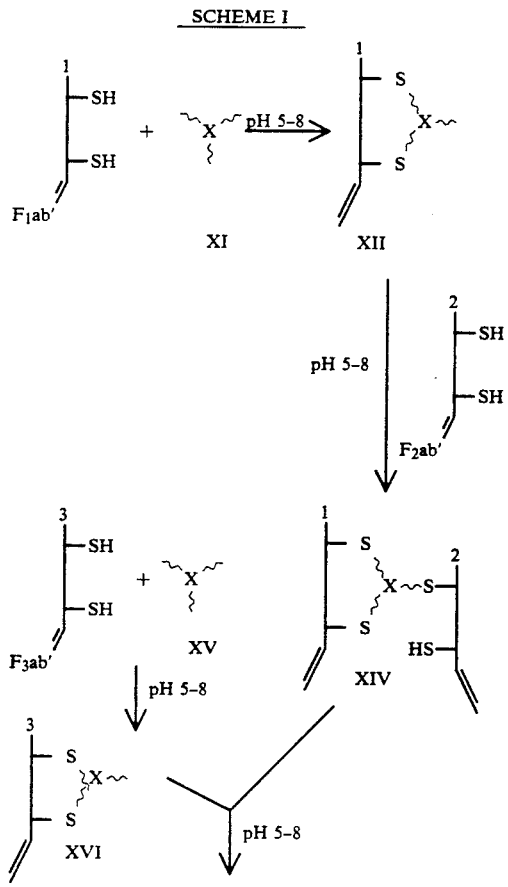

SCHEME I

-continued
SCHEME I

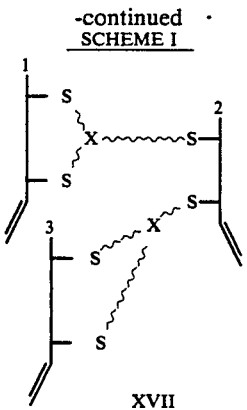

The trivalent coupling agent of the present invention can be synthesized from a variety of compounds acting as the central moiety. Preferably, the compound acting as the central moiety "X" has three chemical functional groups that are capable of binding a maleimide moiety either directly or indirectly. Suitable chemical functional groups include alcohols, aldehydes, carboxylic acids, esters, amides, amines and the like. The central moiety "X" may be directly bound to the three chemical functional groups (e.g., 1,3,5-benzene tricarboxylic acid). Alternatively, the central moiety may contain one or more carbon, nitrogen, oxygen, sulfur or phosphorus atoms, that act as linkers between the central moiety and the three chemical functional groups. For example, in tris(2-aminoethyl)amine, the three $C_2$ (ethyl) chains act as arms between the central moiety, an amino nitrogen, and the three-$NH_2$ groups at their terminus. In its simplest mode, the trifunctional coupling agent of the present invention is synthesized from a triamino compound, such as tris(2-aminoethyl)amine, and N-methoxycarbonylmaleimide.

The trivalent coupling agent of the present invention can have a variety of arm lengths that depend upon both the steric requirements of the Fab'-like fragments being linked and the conformational requirements of the trifunctional antibody-like compound ultimately being synthesized. In general, slightly longer linker arms are preferred in the synthesis of trifunctional antibody-like compounds than in the synthesis of bifunctional antibody-like compounds. The longer linker arms apparently reduce steric hinderance in the hinge region allowing access to underivatized sulfhydryls during additions of the Fab'-like fragment with its third specificity.

Typical compounds used to increase the length of the linker arms are the alpha and omega terminated diamines and/or dithiols. Of these, the alpha and omega terminated dithiols are preferred. By "alpha and omega terminated diamines" as used herein is meant diamines of the formula:

$H_2N—(CH_2)_x—NH_2$ wherein the subscript "x" is an integer ranging from 2 to about 20. By "alpha and omega terminated dithiols" as used herein is meant dithiols of the formula:

$HS—(CH_2)_t—SH$ wherein the subscript "t" is an integer ranging from 2 to about 20.

The alpha and omega terminated dithiols are preferably used to increase the length of a linker arm of the trivalent coupling agent of the present invention after it has already been coupled to its first Fab'-like fragment. This is particularly important where the maleimide is bound to an expensive Fab' fragment and it is determined that a subsequent reaction of the maleimide with a second Fab' fragment is sterically hindered. This utility and the method of combining is reflected in Scheme II. For example in Scheme II, an excess amount of the trivalent coupling agent of the present invention XX is reacted at pH 5-8, preferably pH 5-7, with a Fab'-like fragment XXI, having two free sulfhydryl groups, to form a compound XXII having a single maleimide moiety available for further coupling. To further increase the length of the uncoupled linker arm on XXII, an excess amount of an alpha and omega terminated dithiol XXIII, as defined herein, is reacted with the maleimide moiety of XXII to form the omega terminated thiol XXIV. Reaction at pH 5-8, preferably pH 5-7 of the thiol XXIV with an excess of a bis-maleimide type compound XXV, such as p-phenylenedimaleimide, produces a coupling agent complex XXVI having an extended linker arm with a reactive maleimide moiety at its terminus. The complex of XXVI is analogous to the complex XXII. However, the former's longer linker arm serves to minimize or eliminate any stearic hinderance associated with the coupling agent's binding of the first Fab'-like fragment.

As a practical matter, a trivalent coupling agent of the present invention that has short linking arms selectively couples to a single Fab'-like fragment having two free —SHs in high yield. However, subsequent coupling is sterically hindered, and thus prevented, until the length of the uncoupled arm is increased so as to reduce or eliminate the steric hinderance. Once the length of the linker arm is increased such as described in Scheme II, the second Fab'-like fragment can be selectively coupled.

Thus, the present invention also encompasses a method for extending the length of one of the linker arms of the compound of Formula I, which method comprises:

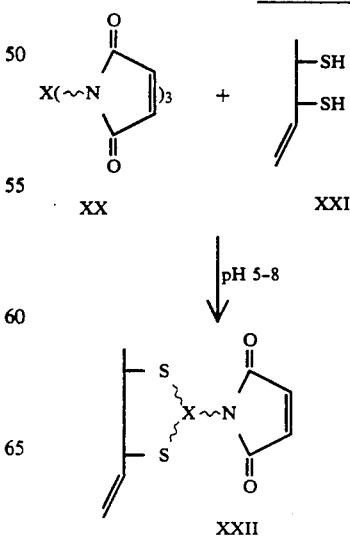

-continued
SCHEME II

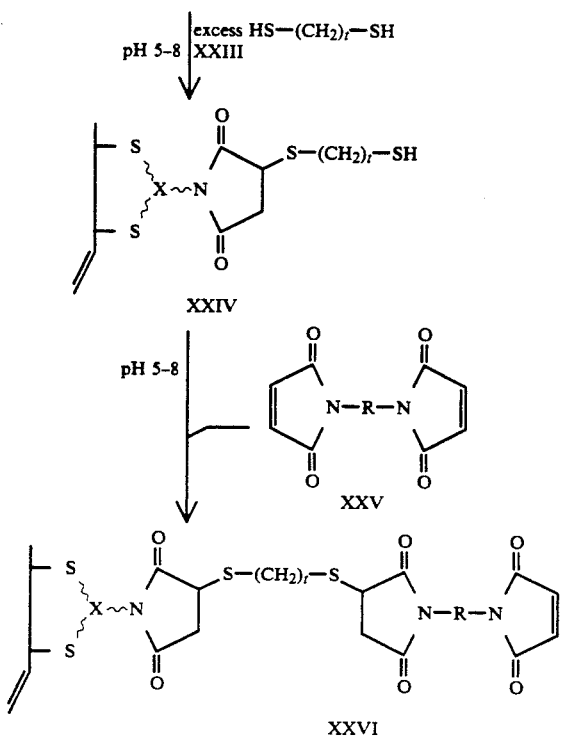

(a) combining the compound of Formula I at pH 5-8 with an Fab'-like fragment having at least 2 free sulfhydryl groups, whereby a maleimide-Fab' complex having a single reactive maleimide moiety is formed;

(b) combining the maleimide-Fab' complex from Step (a) at pH 5-8 with a compound of the formula:

   II wherein the subscript "t" is an integer from 2 to about 20, the compound of Formula II being combined in an amount effective to prevent intermolecular crosslinking between the Fab'-maleimide complexes, the combination forming a coupled product between the maleimide-Fab' complex and the compound of Formula II, the coupled product having an extended linker arm with an —SH moiety extending distally therefrom; whereby said single reactive maleimide moiety becomes coupled to one of the —SH moieties on the compound of Formula II, forming a maleimide-Fab' complex with a single extended linker arm. Although, the couplings in Steps (a) and (b) above may be performed at pH 5-8, they are preferably performed at pH 5-7.

In Step (b), the amount of the compound of Formula II that is effective to prevent intermolecular crosslinking between molecules of the maleimide-Fab' complex is dependent upon a number of factors, including the size of the compound of Formula I, and the size of the integer "t" in Formula II. Typically, increasing molar ratios of the compound of Formula II relative to the maleimide-Fab' complex result in decreasing intermolecular crosslinking of the complex by the compound of Formula II. One skilled in the art can determine the minimum mole ratio of the compound of Formula II relative to the maleimide-Fab' complex to prevent crosslinking of the maleimide-Fab' complex. Preferably, however, a 10 fold or greater molar excess of the compound of Formula II is employed in Step (b) to prevent crosslinking.

The present invention also encompasses the above method further comprising the step of:

(c) combining the coupled product of Step (b) at pH 5-8, preferably 5-7, with an amount of a bis-maleimide effective to prevent intermolecular crosslinking between molecules of said coupled product, whereby a maleimide-Fab' complex that has an extended linker arm with a reactive maleimide at its terminus is formed.

By "bis-maleimide" as used in Step (c) above is meant a compound having a maleimide moiety at each of two termini. Typical bis-maleimides include N,N'-o-phenylenedimaleimide, N,N'-p-phenylenedimaleimide, and N,N'-(oxydimethylene)dimaleimide, which compounds are well known in the art. See, for example, Weston et al., Biochemica et Biophysica Acta, 612: 40–49 (1980). Preferred bis-maleimides include N,N'-bis(-maleimidopropionyl)-2-hydroxy-1,3-propanediamine ("BMP") and bis-(maleimido)-methyl ether ("BMME"). BMP is commercially available from Sigma Chemical Co., St. Louis, Mo., and BMME is commercially available from Boehringer Mannheim Corp., Indianapolis, Ind.

In Step (c), the amount of bis-maleimide that is effective to prevent intermolecular crosslinking between molecules of the "coupled product" is dependent upon a variety of factors. Generally, increasing molar ratios of the bis-maleimide relative to the coupled product of Step (b) result in decreasing intermolecular crosslinking of the coupled product by the bis-maleimide. To determine the minimal amount of bis-maleimide necessary to prevent crosslinking, one skilled in the art can run a series of reactions with increasing molar ratios of bis-maleimide relative to coupled product until significant crosslinking is no longer observed. Preferably to avoid crosslinking, one simply employs a 10 fold or greater molar excess of bis-maleimide relative to coupled product.

As previously discussed herein, Fab'-like fragments having at least two free sulfhydryls are derived from mouse $IgG_1$, $IgG_{2a}$, and $IgG_{2b}$; human IgG; and primate (e.g., chimp) IgG.

The lability of all three of the linker arms on the trivalent coupling agent of the present invention are increased when a labile chemical functional group, such as a disulfide (—S—S—) is symmetrically introduced into each arm. Chemical reactions symmetrically introducing a —S—S— moiety into each linker arm are well known to those skilled in the art. In order to selectively increase the lability of a single linker arm, a labile bond, preferably a —S—S—, must be selectively incorporated into the single linker arm. Selective incorporation is best achieved after an initial coupling between a trivalent coupling agent of the present invention and an Fab'-like fragment having two free sulfhydryls. As a result of this coupling, there remains a single terminal maleimide moiety for further reaction. The labile disulfide linkage (—S—S—) is then incorporated into the uncoupled linker arm via an alpha-omega diamine or more preferably an alpha-omega dithiol like compound that contains a disulfide moiety therein. The alpha-omega dithios having a disulfide therein are performed over the corresponding diamines due to the minimization of undesirable side reactions with the free amines on the Fab' like fragments at the reaction pH.

By way of example, disulfide containing dithiols and diamines are compounds of the respective formulas:

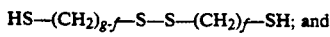

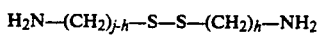

wherein g and j are integers from 2-18 and f and h are integers from 2-18 with the proviso that the sum of g and f and/or j and h is not greater than 20. Selective incorporation of a disulfide containing dithiol into a single linker arm at pH 5-8, preferably pH 5-7, is preferably accomplished via the reaction sequences already provided in Scheme II.

The following examples are given by way of illustration only and should not be construed as limiting the invention in spirit and/or scope.

DESCRIPTION OF THE PREFERRED EMBODIMENT

EXAMPLE 1

Preparation of N-Methoxycarbonylmaleimide

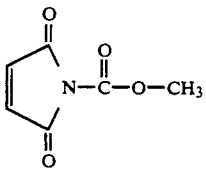

To a 1000 ml 3-neck round bottom flask was added 400 ml of ethyl acetate. The flask was placed in an ice bath and the temperature was allowed to drop to about 0° C. To the cooled flask was sequentially added with stirring 7.76 g of maleimide and 8.8 ml of N-methylmorpholine. Then, through an addition funnel was added to the stirring mixture 6.26 ml of methyl chloroformate at a rate so as not to raise the temperature above 3° C. Through the addition funnel was then added 5 ml of ethyl acetate as washing and the washing was added to the reaction mixture. The reaction mixture was stirred for 30 minutes at between 0°-3° C. Thereafter, the reaction mixture was filtered through a Buchner funnel. The flask was washed 2× with 10 ml of ethyl acetate and the washings were also filtered. The resulting precipitate was washed 2× with 10 ml of ethyl acetate. The combined filtrate and washings were extracted with 100 ml of ice cold water, dried (10 g Na$_2$SO$_4$), and evaporated to dryness under reduced pressure. The residue was redissolved in 50-100 ml of ethyl acetate:isopropyl ether (40:60 /v:v) using a water bath at 60° C. The resulting solution was filtered, cooled until crystals appeared. After 30 minutes in an ice bath, the cooled solution and crystals were filtered through a sintered glass funnel and the crystals washed 2× with 20 ml of isopropyl ether. The crystals were vacuum dried overnight, M.P. 61°-63° C.

EXAMPLE 2

Tris-(2-N-maleimidoethyl)amine ("TMA")

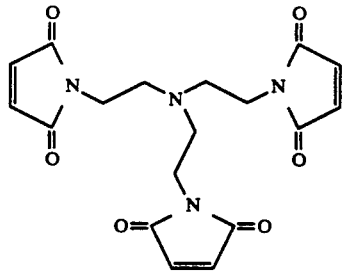

To 15 g of NaHCO$_3$ in a 250 ml Erlenmeyer flask was added 100 ml of cold water and the mixture was stirred in an ice bath until the reaction mixture was at 0° C. To 80 ml of the supernatant solution in a 100 ml round bottom flask was added 1.8 ml of tris(2-aminoethyl)amine and the mixture was cooled 0° C. in an ice bath. To the cooled reaction mixture was added with stirring 6.2 g of finely ground N-methoxycarbonylmaleimide and the mixture was stirred for an additional 10 minutes in the ice bath. Thereafter, 240 ml of water was added to the mixture and it was stirred at room temperature for 30 minutes. Then, the pH of the solution was adjusted to between pH 6-7 with concentrated HCl and the volume was reduced to 100 ml by evaporation under reduced pressure. The pH of the resulting solution was adjusted to 10 with saturated Na$_2$CO$_3$ solution. The resultant solution was extracted 3× with 200 ml of ethyl acetate and the combined organic phases were washed 2× with 100 ml of H$_2$O. The organic phase was dried (30 g Na$_2$SO$_4$), filtered and evaporated under reduced pressure to dryness. The residue was dissolved in 40 ml of warm ethyl acetate, filtered (Buchner funnel), and evaporated under reduced pressure to dryness. The residue was dissolved at a ratio of 5 ml/g (residue) in ethyl acetate:methylene chloride (1:3/v:v). To a 150 ml Lobar silica gel column that had been pre-equilibrated with 2 bed volumes of ethyl acetate:methylene chloride (1:3/v:v) was added a 5 ml aliquot of the dissolved residue. The column was eluted with the same solvent at 4 ml/min and the TMA fraction, as monitored at A$_{280}$, was collected in a 500 ml round bottom flask. The TMA fraction was evaporated to dryness. Additional 5 ml aliquots of the dissolved residue were similarly treated and the corresponding TMA fractions were evaporated by dryness. The TMA residues were dissolved in 10 ml of the elution solvent, pooled together and evaporated under reduced pressure to dryness. The combined residue was dissolved in 40 ml of ethyl acetate:isopropyl ether (3:1/v:v) using a 60° C. water bath, filtered, and cooled sufficiently until the TMA precipitated out as crystalline yellow needles. The resultant TMA crystals were collected on a sintered glass funnel, washed 2× with 5 ml of isopropyl ether, and dried overnight under vacuum, M.P. 132°-133° C.

Analysis for C$_{18}$H$_{18}$N$_4$O$_6$ (MW=386.36). Calcd: C, 55.95; H, 4.70; N, 14.50. Found: C, 55.54; H, 4.69; N, 14.45.

$^1$H NMR $\delta_{TMS}$ CDCl$_3$ (300 MHz): 6.65(6H,s); 3.49(6H,t); and 2.68(6H,t).

I.R. (KBr): 1700 cm$^{-1}$ (C=O).

U.V. (DMF): peak at 272, molar extinction coefficient=1920.

EXAMPLE 3

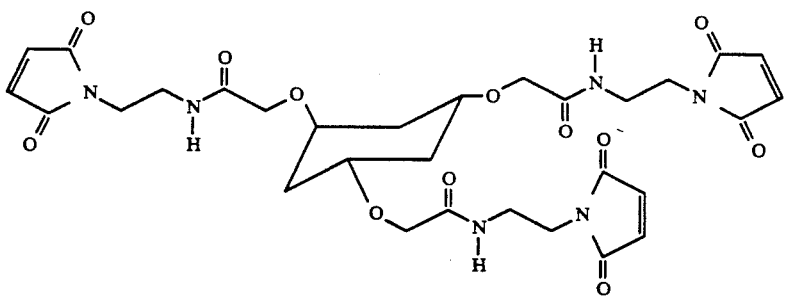

One mole of cyclohexan-1,3,5-triol is reacted with 3 moles of $BrCH_2COO^-K^+$ in tetrahydrofuran in the presence of 3 eq. of potassium t-butoxide at 22° C. for 1 hr. The resulting tricarboxylic acid is then reacted with N-hydroxysuccinimide (NHS) and dicyclohexylcarbodiimide (DCC) for 1 hr. at 0° C. in tetrahyrafuran to yield the tris-succinimide. This compound will then react with a 10 fold excess of ethylenediamine in saturated sodium bicarbonate for 1 hr. at 22° C. The resultant compound is then reacted with N-methoxycarbonylmaleimide (whose synthesis is described in Example 1) in saturated sodium bicarbonate at 0° C. for 10 minutes yielding a tris-maleimide in which the X component of Compound I is a cyclohexyl moiety.

ysuccinimide in the presence of dicyclohexylcarbodiimide at 0° C. for 1 hr. followed by incubation for 3 hrs. at room temperature to yield the succinimide esters of the previously mentioned acid. The succinimide ester compound is then reacted with tris(2-aminoethyl)amine in dimethylformamide (DMF) at room temperature for 4 hr. to produce the tris-maleimido compound, having the structure shown above. Throughout the above described reactions, the initial stereo chemistry of the amino acid starting material is maintained about its asymmetric center (*). Hence, by selection of L-serine or D-serine, L or D stereochemistry respectively is maintained about each asymmetric center.

EXAMPLE 5

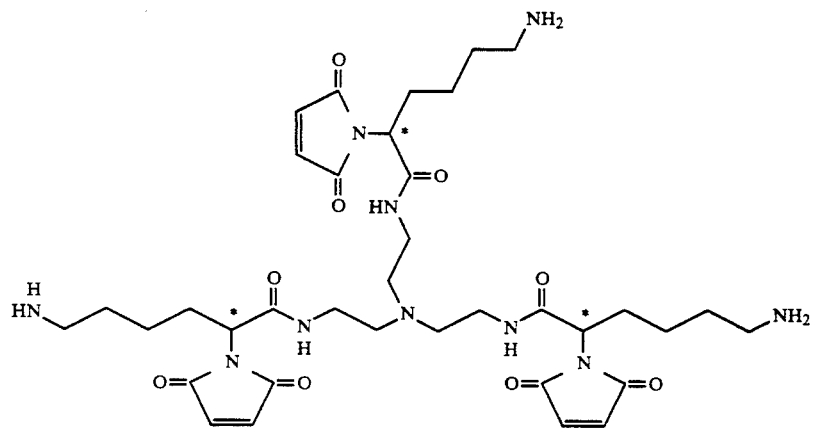

EXAMPLE 4

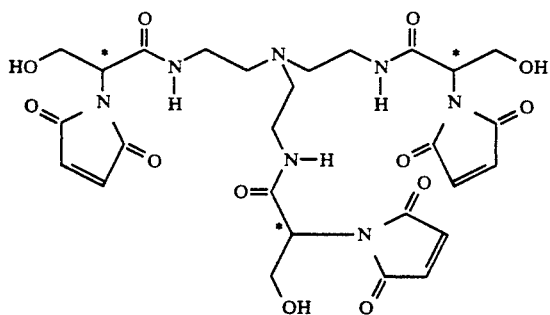

To 1 mole of serine in aqueous solution in the presence of $NaHCO_3$ at 0° C. is added 1.1 moles N-methyoxycarbonylmaleimide. The reaction is allowed to proceed at 0° C. for 10 minutes followed by a 30 minute incubation at room temperature. The resulting product, 2-(N-maleimido)-3-hydroxypropanoic acid, is then reacted in diglyme with a 10% molar excess of N-hydrox- To an aqueous bicarbonate solution which has been cooled to 0° C. is added lysine in which the terminal amino group is protected by a t-butoxycarbonyl (BOC) group. To this is then added approximately equimolar amounts of N-methoxycarbonylmaleimide. The reaction is allowed to proceed for 10 min. at 0° C. followed by a second incubation at room temperature for 30 min. The resultant α-maleimido carboxylic acid is then be reacted in tetrahydrofuran with a 10% molar excess of N-hydroxysuccinimide in the presence of N,N-dicyclohexylcarbodiimide at 0° C. for 1 hr. followed by an incubation at room temperature for 3 hrs. to yield the succinimide ester of the aforementioned acid. The succinimide ester is then reacted with tris(2-aminoethyl)amine in dimethylformamide (DMF) for 4 hrs. at room temperature to yield a tris-maleimide compound wherein the terminal amine still bears the BOC protecting group. Removal of the BOC group is accomplished by hydrolysis for 1 hr with 3M HCl in ethyl acetate at room temperature. As in Example 4, stereochemistry about the asymmetric center (*) in the lysine starting material is retained in the final product.

EXAMPLE 6

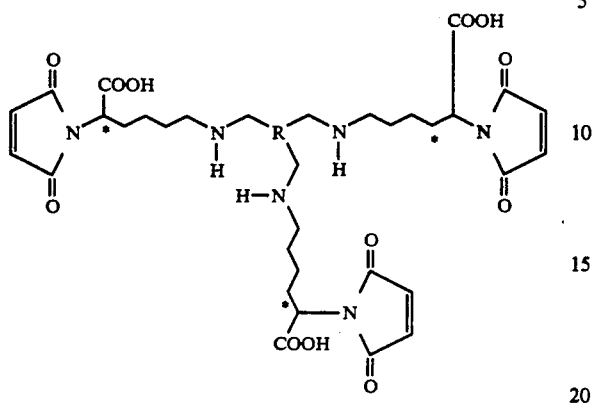

To an alpha amino acid such as lysine, in which the terminal amino group is free and the alpha amino group is protected by a phenoxycarbonyl (POC) group, is condensed a trialdehyde compound of the formula R(CHO)$_3$ in the presence of NaBH$_3$CN. The POC protecting groups on the resultant tricondensation product are removed by hydrogenation over Pd/C. The resulting deprotected alpha amino groups of the tricondensation product are now suited for reaction with N-methoxycarbonyl maleimide. The tricondensation product is dissolved in aqueous bicarbonate at about 0° C. To this is added N-methoxycarbonylmaleimide and the temperature is maintained at 0° C. for 10 min. Thereafter, the reaction is allowed to proceed at room temperature for 30 min. The resultant maleimide is then purified as described for TMA (Example 2 herein). As for Examples 5 and 6, any stereochemistry about the asymmetric center (*) in the lysine starting material is retained in the final product.

EXAMPLE 7

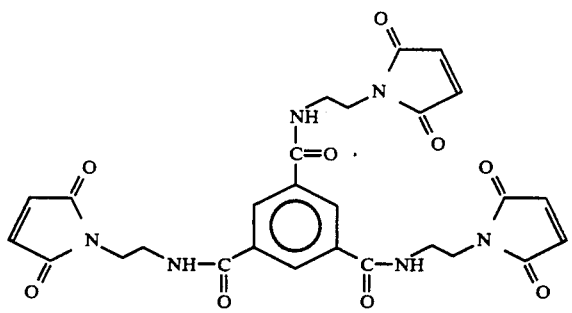

To 1,3,5-benzene tricarboxylic acid in tetrahydrofuran (THF) at 0° C. is added a 10% equivalent excess of N-hydroxysuccinimide in the presence of dicyclohexylcarbodiimide. The reaction mixture is maintained at 0° C. for 1 hour followed by an incubation for 3 hr. at room temperature to yield the tris-succinimidyl ester of the triacid.

In a separate reaction, ethylene diamine is reacted according to the procedure in Example 2 with an equimolar amount or less of N-methoxycarbonylmaleimide, which is prepared according to the procedure in Example 1. The resulting product, 2-N-maleimidoethylenediamine, is then reacted with the tris-succinimidyl ester from above in a saturated sodium bicarbonate solution for about 1 hr. at 22° C. to produce the tris-maleimide corresponding to the chemical formula shown above.

EXAMPLE 8

Tris[2-N-(maleoylglycyl)aminoethyl]amine ("TMG")

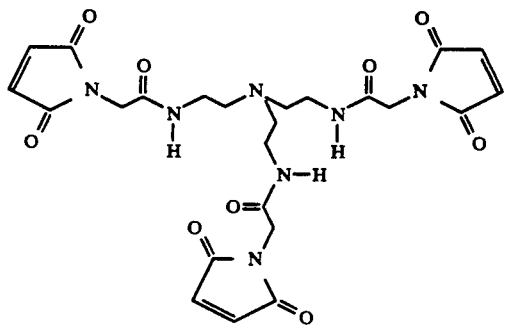

Glycine (1.5 g, 20 mmol) in saturated NaHCO$_3$ (100 ml) was vigorously stirred at 0° C. with finely ground N-methoxycarbonylmaleimide (3.1 g, 20 mmol). After 10 minutes the solution was diluted with 400 ml of water and stirred at room temperature for 40 min. The pH of the solution was adjusted to ~7 with concentrated HCl and the neutralized solution was evaporated in vacuo to about 50 ml. Thereafter, the solution was acidified to pH ~2 with 3N HCl and extracted two times with 100 ml of ethyl acetate. The combined ethyl acetate extract was washed with water, dried over anhydrous Na$_2$SO$_4$ and evaporated to dryness. The crude product was dissolved in 5 ml of CH$_2$Cl$_2$:CH$_3$COOH/95:5 and passed through a silica gel flash column (60 g) eluted with the same solvent. After evaporation of the organic solvent, the product was lyophilized to yield 1.85 g of fluffy white maleoylglycine.

$^1$H NMR (D$_2$O): δ4.30(2H, s), and 6.95(2H, s).

IR (KBr) 1710 cm$^{-1}$ (C=O)

Maleoylglycine (1.55 g, 10 mmol) in 50 ml of diglyme was treated at 0° C. with N-hydroxysuccinimide (1.27 g, 11 mmol) and dicyclohexylcarbodiimide (2.23 g, 11 mmol). After 1 hour at 0° C. and 3 hours at room temperature, the reaction mixture was filtered and evaporated to dryness to yield 1.9 g of crude maleoylglycine N-succinimidyl ester.

Maleoylglycine N-succinimidyl ester (1.9 g, 7.5 mmol) was dissolved in 35 ml of DMF, and tris(2-aminoethyl)amine (329 mg, 2.25 mmol) in 10 ml of dimethylformamide (DMF) was added dropwise with stirring to the solution. The reaction was monitored by reverse phase (C$_{18}$) high pressure liquid chromatography (HPLC) eluted with a linear gradient from 80% 0.1M ammonium acetate (pH 5)/20% CH$_3$OH to 50% 0.1M ammonium acetate (pH 5)/50% CH$_3$OH. The reaction solution was concentrated and the crude product ("TMG") was divided into three portions and purified on a 150 ml Lobar reverse phase C$_{18}$ column eluted with a step gradient from 20% CH$_3$OH/80% 0.1M ammonium acetate, pH 5 to 50% CH$_3$OH/50% 0.1M ammonium acetate.

$^1$H NMR (DMF): δ2.50(6H); 3.18(6H); and 7.05(6H).

EXAMPLE 9

Tris[2-N-(maleoylglycylglycyl)aminoethyl]amine ("TMGG")

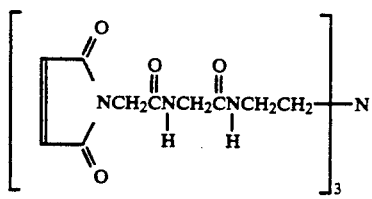

To 660 mg of glycylglycine (5 mmol) in 25 ml of saturated NaHCO$_3$ at 0° C. was added 775 mg of N-methoxycarbonylmaleimide (5 mmol) with vigorous stirring. After 10 minutes, the solution was diluted with 100 ml of water and stirred at room temperature for 30 minutes. The pH of the solution was adjusted from 8 to 6.3 with 3N HCl and the solution was evaporated with rotation under reduced pressure ("rotavaped") to approximately 20 ml. The concentrated solution was acidified to pH 2 with 3N HCl and extracted two times with 50 ml of ethyl acetate. The combined ethyl acetate extract was dried over anhydrous Na$_2$SO$_4$ and evaporated to dryness in vacuo.

The resulting residue was dissolved in 18 ml of diglyme and treated at 0° C. with N-hydroxysuccinimide (460 mg, 4 mmol) and dicyclohexylcarbodiimide (824 mg, 4 mmol). After stirring 1 hour at 0° C. and 2 hours at room temperature, the reaction mixture was filtered and the filtrate was evaporated to dryness to yield 3.2 mmol maleoylglycylglycine N-succinimidyl ester.

To 66 mg of tris(2-aminoethyl)amine (0.45 mmol) in 2 ml of dimethylformamide ("DMF") was added dropwise with stirring 8 ml of 0.2M maleoylglycylglycine N-succinimidyl ester in DMF. After stirring at room temperature for 1 hr., the solution was rotavaped to 3 ml and passed through a silica gel flash column (60 g) eluted sequentially with (1) 150 ml EtOAc:MeOH/90:10; (2) 150 ml EtOAc:MeOH/75:25; (3) 150 ml EtOAc:MeOH/50:50; and (4) 150 ml MeOH. After evaporation of the solvent, 0.22 g of TMGG as a light yellow residue was obtained from fraction 3.

$^1$H NMR (DMF): δ2.55(6H); 3.25(6H); 3.95(6H); 4.35(6H); and 7.10(6H).

EXAMPLE 10

Preparation Of Antibodies (a) Anti-In-EDTA ("CHA")

The antibody herein designated as "CHA" is a monoclonal anti-hapten antibody having specificity for the complex formed between ethylenediaminetetraacetic acid ("EDTA") and the indium (III) ion. For imaging purposes, the $^{111}$In isotope of indium (III) is used. In the present invention, the EDTA derivative, ethanolaminethioureabenzyl EDTA ("EOTUBE") was used as the chelating agent. The CHA 255 antibody was prepared as follows. Spleen cells from BALB/c mice multiply immunized with the antigen were fused with a variant of the P3.653 myeloma cell line. See Gerhard, *Monoclonal Antibodies*, edited by Kenneth et. al., Plenum Press, New York (1980). The resulting hybridomas were screened by a solid phase second antibody radioimmunoassay for their ability to binding indium aminobenzyl-EDTA (Wang et. al., *Journal of Immunological Methods*, 18, 157 (1977)). Based on their high titers and relatively high affinity as determined by inhibition of binding by unlabeled antigen, a monoclonal antibody designated as CHA 255 was chosen for further study and injected intraperitoneally into BALB/c mice for ascites production. The monoclonal antibodies were purified from mouse ascites by ion-exchange chromatography on DEAE-cellulose as described by Parham et. al., *J. Immunol. Meth.*, 53, 133 (1982). Monoclonal antibody CHA 255 is further described by Reardon, D. T., et. al., *Nature*, 316, p. 265-268 (1985) and Meares et. al., U.S. Pat. No. 4,722,892, issued Feb. 2, 1988, herein incorporated by reference. Hereinafter, the CHA 255 antibody is referred to as "CHA."

(b) Anti-Y-DTPA ("CYA")

The antibody designated herein as "CYA" is a monoclonal anti-hapten antibody having specificity for the complex formed between the chelating agent, diethylenetriaminepentaacetic acid ("DTPA"), and the yttrium (III) ion. For therapeutic purposes the $^{90}$Y isotope of yttrium (III) is used. For enhanced pharmaceutical acceptability, the methylthioureabenzyl derivative of DTPA, which is known as methylthioureabenzyldiethylenetriaminepentaacetic acid ("MeTUBD") is used. The CYA316 antibody (hereinafter "CYA") was prepared using the general techniques described in Reardon, et al., "Antibodies Against Metal Chelates," *Nature*, 316: 265-267 (1985) and in Meares, et al. (U.S. Pat. No. 4,722,892), the latter being incorporated herein by reference.

(c) Anti-CEA ("ZCE")

The antibody designated herein as "ZCE" is a monoclonal antibody having specificity for carcinoembryonic antigen. The "ZCE" antibody is commercially available from Jean Pierre Mach, University of Lausanne, Lausanne, Switzerland.

(d) Chimeric Anti-CEA ("xCEM")

The antibody designated herein as "xCEM" is a mouse/human chimeric antibody having specificity for carcinoembryonic antigen. The "xCEM" antibody was cloned and expressed according to the procedure taught in Biedler et al., *J. Immunol.*, 141: pp. 4053-4060 (1988).

(e) Chimeric Anti-In-EDTA ("xCHA")

The antibody designated herein as "xCHA" is a mouse human chimeric antibody having specificity for the In-EDTA chelate complex. The "xCHA" antibody was prepared by essentially the same method used for the preparation of "xCEM" above (i.e., *J. Immunol.*, 141: pp. 4053-4060 (1988)) except that in the preparation of "xCHA," the variable regions from the murine antibody CHA-255 were used instead of the variable regions from the murine antibody CEM-231. The synthesis of xCHA is further described in U.S. patent application Ser. No. 07/274,106, by M. J. Johnson, filed Nov. 17, 1988, herein incorporated by reference, and was described in a presentation to the 7th International Congress of Immunology, Berlin, Aug. 1, 1989.

EXAMPLE 11

Preparation Of The Bifunctional Antibody-Like Compound xCEM-TMA-xCEM (a) Preparation of xCEM-Fab'SH A chimeric monoclonal antibody to carcinoembryonic antigen (CEA) and designated as "xCEM" was digested with pepsin using the conventional technique described in Example 12(a) herein, except that the digestion was for only 3 hours. (See, also for example, U.S. Pat. No. 4,659,839, Nicoletti et al., which details pepsin digestion and is incorporated herein by reference.) The digested xCEM was then dialyzed overnight against borate buffer, pH ~8 (by paper). The absorbance of the dialyzed pepsin digestate was measured at 280 nm ("$A_{280}$") which indicated 3.9 mg/ml of protein. To 900 μl of the dialyzed xCEM digestate was added 2 μl of 0.5M diethylenetriaminepentaacetic acid (DTPA) and the mixture was incubated at 37° C. for 15 minutes. Thereafter, 36 μl of 0.5M cysteine (Cys) was added to the mixture which was incubated for a further 10 minutes at 37° C. The resultant reaction mixture was applied to a Biogel P-6 column (Biorad Laboratories, Richmond, Calif. 94804) and 2.0 ml of a protein fraction were collected. The fraction's $A_{280}$ indicated a 1.3 mg/ml or 26 μM concentration of the Fab'-like fragment designated as xCEM-Fab'SH. The concentration of sulfhydryl groups in the fraction was determined using the standard technique of adding a molar excess of 5,5'-dithiobis-(2-nitrobenzoic acid) (i.e., DTNB) plus borate buffered saline (50 mM sodium borate, 50 mM NaCl, pH 8.2) to an aliquot of the fraction and measuring the absorbance difference at 412 nm between the DTNB containing aliquot and a blank. Using this technique, the number of sulfhydryl groups per Fab' fragment was calculated to be 1.5, indicating approximately 1.5 sulfhydryl groups per xCEM-Fab'SH.

(b) Coupling Tris-(2-N-maleimidoethyl)amine With xCEM-Fab'SH

To 1.0 mg of tris-(2-N-maleimidoethyl)amine (i.e., "TMA") dissolved in 80 μl of dimethylformamide was added 1 ml of the eluate containing xCEM-Fab'SH from above. The reaction mixture was allowed to stand at room temperature for 10 minutes. Thereafter, to separate the TMA derivatized Fab' fragment from the TMA, the reaction mixture was applied to a Biogel P-6 column (Biorad Laboratories, Richmond, Calif. 94804) and eluted in citrate buffered saline (50 mM ammonium citrate, 100 mM NaCl, 1 mM DTPA, pH 6.3) and eluted into 0.1M NaCl at 1~DTPA, pH 6-3 50 mM ammonium citrate to 0.1 mole NaCl and 1 mM pH 6.3. 2.3 ml fraction of protein containing eluate was collected. The $A_{280}$ indicated the concentration of the desired product to be 0.49 mg/ml or 9.8 μM (assuming no absorbance of TMA). The corresponding maleimide concentration in the coupled product was determined to be 4.6 μM, resulting in 0.47 TMA molecules per Fab' fragment. The resultant coupled product is designated herein as "xCEM-Fab'-TMA."

(c) Coupling xCEM-Fab'-TMA With xCEM-Fab'SH To Form xCEM-TMA-xCEM

The products from (a) and (b) above were combined in model reactions in the following ratios to test the coupling properties of TMA derivatized Fab'-like fragments. The product of these reactions was designated as xCEM-TMA-xCEM (the "Fab'" having been deleted for clarity):

| xCEM-Fab'-TMA .49 mg/ml | xCEM-Fab'SH (1.3 mg/ml) | Molar Ratio |
| --- | --- | --- |
| 300 μl | 115 μl | 1:1 |
| 300 μl | 57 μl | 2:1 |
| 150 μl | 115 μl | 1:2 |

The yields of the model compound, xCEM-TMA-xCEM, varied as a function of the ratio of the reactants:

| CEM-Fab'-TMA/CEM-Fab'SH (Molar Ratio) | % Yield Of (CEM-Fab')$_2$TMA |
| --- | --- |
| 2:1 | 46% |
| 1:1 | 40% |
| 1:2 | 19% |

Thus, the best yields of xCEM-TMA-xCEM were obtained when the Fab'-like fragments bearing the maleimide moiety were in excess over the Fab'-like fragments containing the free sulfhydryl group.

EXAMPLE 12

Preparation Of The Bifunctional Antibody-Like Compound, xCHA-TMA-xCEM, Having Specificity For The Imaging Agent, In-EDTA, and CEA (a) Preparation Of F(ab')$_2$ Fragments From Intact Antibody.

Unless otherwise described herein, the monoclonal antibodies designated as xCHA, CHA, CEM, ZCE and CYA herein were digested with pepsin to produce F(ab')$_2$ fragments according to the following procedure. Antibody solutions, having an antibody concentration of 5–15 mg/ml as determined by their absorbance at 280 nm ("$A_{280}$"), were dialyzed in acetate buffered saline (0.1M sodium acetate, 0.1M NaCl, pH 4.1) overnight at 4° C. Thereafter, a concentrated pepsin solution was added to the dialyzed solution containing approximately 2% antibody by mass in pepsin. The reaction mixture was then incubated from 4–48 hours at 37° C. The reaction was terminated by addition of NaHCO$_3$ until the pH was ~8. The F(ab')$_2$ fragments were purified by a variety of techniques, including gel filtration on a Sephadex ® G-150 column (Pharmacia, Piscataway, N.J.); high pressure liquid chromatography, using as a matrix either Fast Flow S (Pharmacia) or TSK-GEL SP-TOYOPEARL ® 650S cation exchange resin (Tosoh Corp., Japan), and 0.17M sodium acetate pH 4.5 with a NaCl gradient as the elution buffer. After isolation, the F(ab')$_2$ fragment was dialyzed in borate buffered saline (50 mM sodium borate, 50 mM NaCl, pH 8.2). The dialyzed solutions containing F(ab')$_2$ fragments were used in the subsequent reduction steps.

(b) Reduction of xCHA-F(ab')$_2$ to xCHA-Fab'SH

To 4 ml of the above dialyzed solution containing 5.7 mg/ml xCHA-F(ab')$_2$ was added 118 mg of NaHCO$_3$ which adjusted the pH to 8. Thereafter, 8 μl of 0.5M diethylenetriaminepentaacetic acid ("DTPA") was added and the reaction was allowed to proceed at 37° C. for 15 minutes. Upon the further addition of 160 μl of 0.5M cysteine, the reaction mixture was incubated for 10 minutes at 37° C. The reaction mixture was applied to a 50 ml P-6 column (Biorad Laboratories, Richmond, Calif. 94804) that was pre-equilibrated and eluted with citrate buffered saline (50 mM ammonium citrate, 100 mM NaCl, 1 mM DTPA, pH 6.3). During elution, a 7.84 ml protein fraction was collected. The absorbance of the fraction at 280 nm ("$A_{280}$") indicated that the protein concentration of the fraction was 55 μM. The sulfhydryl content of the protein fraction was determined to be 110 μM by adding 5,5'-dithiobis-(2-nitrobenzoic acid) ("DTNB") and borate buffered saline (50 mM sodium borate, 50 mM NaCl, pH 8.2) to an aliquot of the reaction mixture and measuring the absorbance differences at 412 nm between the aliquot containing DTNB and a blank. The mole ratio of sulfhydryl groups to Fab' fragment for xCHA-Fab'SH was calculated to be 2.0:1. The resulting reduced fragment was designated xCHA-Fab'SH.

(c) Preparation Of a F(ab')₂ Fragment From Anti-CEA

A mouse/human chimeric antibody, having specificity for CEA and designated as "xCEM," was cloned and expressed according to the procedure taught in Beidler et al., J. Immunol., 141, pp. 4053–4060 (1988). The "xCEM" antibody was digested with pepsin for 3 hours according to the procedure described in Example 11(a) herein to produce the corresponding F(ab')₂ fragment, designated herein as xCEM-F(ab')₂.

(d) Reduction of xCEM-F(ab')₂ to xCEM-Fab'SH

To 6.5 ml of the final dialyzed solution from step (c) above, which contained 8.46 mg/ml of xCEM-F(ab')₂, was added 13 µl of 0.5M diethylenetriaminepentaacetic acid ("DTPA"). The reaction mixture was incubated for 15 minutes at 37° C. followed by the addition of 260 µl of 0.5M cysteine and a further incubation at 37° C. for 10 minutes. Thereafter, the resultant mixture was applied to a 50 ml Biogel P-6 column (Biorad Laboratories, Richmond, Calif. 94804) which was pre-equilibrated with citrate buffered saline (50 mM ammonium citrate, 100 mM NaCl, 1 mM DTPA, pH 6.3). Upon elution of the column with this same buffer, a 10.8 ml protein fraction was collected. The absorbance of the eluate at 280 nm indicated the protein concentration to be 104 µM. The sulfhydryl content, as determined by the procedure in Example 11(a) herein, was calculated to be 1.6 per fragment. The resulting reduced fragment was designated xCEM-Fab'SH.

(e) TMA derivatization of xCEM-Fab'SH

The reduced fragment, xCEM-Fab'SH, was coupled to tris(2-N-maleimidoethyl)amine ("TMA") according to the following procedure. To 12 mg of TMA dissolved in 200 µl of dimethylformamide (DMF) in a test tube was added 10 ml of citrate buffered saline (50 mM ammonium citrate, 100 mM NaCl, 1 mM DTPA, pH 6.3) that was 104 µM in xCEM-Fab'SH. The mixture turned cloudy at first but cleared when the addition of 10 ml of xCEM-Fab'SH was complete. A white precipitate remained on the bottom and sides of the test tube. The reaction was allowed to stand at room temperature for 10 minutes. Thereafter, the reaction mixture was applied to a 200 ml P-6 column (Biorad Laboratories) that had been pre-equilibrated with citrate buffered saline (50 mM ammonium citrate, 100 mM NaCl, 1 mM DTPA, pH 6.3). Upon elution of the column with the same buffer, a 23 ml fraction containing xCEM-Fab'-TMA was collected. The absorbance of the fraction at 280 nm indicated that its protein concentration was 2.3 mg/ml or 47 µM.

Using maleimide back titration, the maleimide concentration of the protein fraction was also determined. Specifically, to 200 µl of the 23 ml fraction containing xCEM-Fab'-TMA was added 20 µl of 1.0 mM cysteine. The mixture was allowed to stand at room temperature for 5 minutes. Thereafter, 10 µl of 5,5'-dithiobis-(2-nitrobenzoic acid) ("DTNB") and 770 µl of borate buffered saline (50 mM sodium borate, 50 mM NaCl, pH 8.2) were added. The reaction mixture was spectrophotometrically analyzed at 412 nm and the maleimide concentration in the 23 ml fraction was determined to be 34 µM. The mole ratio of available maleimide per xCEM-TMA molecule was calculated to be 0.72.

(f) Conjugation of xCHA-Fab'SH with xCEM-Fab'-TMA

To 7.2 ml (396 nmol) of the 55 µM xCHA-Fab'SH solution from Example 12(b) herein was added with stirring 11.6 ml (545 nmol) of the 47 µM xCEM-Fab'-TMA solution from Example 12(e) above. The ratio of xCHA-Fab'/maleimide in this reaction mixture was calculated to be 1.0:1. The reaction mixture was allowed to stand at room temperature for 4 hours at which time the reaction was stopped by the addition of 20 µl of a 1M solution of the alkylating agent, N-ethylmaleimide ("NEM"). The product, xCHA-TMA-xCEM, was purified from the reaction mixture by a variety of techniques which included HPLC (high pressure liquid chromatography) and using a Fast Flow S (Pharmacia, Piscataway, N.J.) or a TSK-GEL SP-TOYOPEARL® 650s (Tosoh Corp., Japan) matrix; and gel filtration on a Sephadex® G-150 column (Pharmacia, Piscataway, N.J.). Those skilled in the art are familiar with protein separation techniques involving HPLC, and gel filtration.

EXAMPLE 13

Preparation Of The Bifunctional Antibody-Like Compound, ZCE-BMP-CHA, Having Specificity For CEA And In-EDTA (a) Preparation Of The F(ab')₂ Fragment Of Anti In-EDTA The antibody to In-EDTA, designated herein as CHA, was digested with pepsin according to the procedure in Example 12(a) to produce its corresponding F(ab')₂ fragment, CHA-F(ab')₂.

(b) Reduction of CHA-F(ab')₂ to CHA-Fab'SH

A 5 ml aliquot of a final dialyzed solution from step (a) above, which contained 10 mg/ml CHA-F(ab')₂, was reduced and purified on a P-6 column (Biorad Laboratories, Richmond, Calif. 94804) according to the procedure in Example 12(b). Upon elution of the P-6 column (Biorad Laboratories), a 12 ml protein fraction was collected. Based upon the absorbance of the fraction at 280 nm, the concentration of the F(ab') fragment was 86 µM. The sulfhydryl concentration of the protein fraction was determined to be 163 µM using 5,5'-dithiobis-(2-nitrobenzoic acid) ("DTNB"). The molar ratio of sulfhydryl groups to Fab' fragments for CHA-Fab'SH was calculated to be 1.9:1.

(c) BMP Derivatization of CHA-Fab'SH

To 1 ml of a 50:50 solution of DMF/H₂O was added 13 mg of N,N'-bis(3-maleimidopropionyl)-2-hydroxy-1,3-propanediamine (hereinafter "BMP") which is commercially available from Sigma Chemical Co., St. Louis, Mo. After dissolution of the BMP, 12 ml of the 86 µM protein fraction from step (b) above, which contained CHA-Fab'SH, was added to the BMP solution. The reaction mixture was allowed to stand for 10 minutes at room temperature. Thereafter, the reaction mixture was applied to and eluted from a 200 ml P-6 column (Biorad Laboratories) with citrate buffered saline (50 mM ammonium citrate, 100 mM NaCl, 1 mM DTPA, pH 6.3). A 27 ml protein fraction, which contained the CHA-Fab'BMP, was collected. The $A_{280}$ indicated the CHA-Fab'BMP concentration to be 33 µM.

The maleimide content of the protein fraction was determined on a 300 µl aliquot of the above fraction using 20 µl of 1 mM cysteine, 10 µl of 5,5'-dithio-bis-(nitrobenzoic acid) ("DTNB"), and 670 µl of borate buffered saline pH 8.2, as described in Example 12(e) herein. The maleimide content of the fraction was determined to be 33 μM. The number of maleimide moieties available per xCHA-Fab' was calculated as 1.0.

(d) Reduction of ZCE-F(ab')$_2$ to ZCE-Fab'SH

A commercially available monoclonal antibody to CEA, licensed from Jean Pierre Mach, University of Lausanne, Lausanne, Switzerland, and designated herein as ZCE, was digested with pepsin according to the procedure in Example 11(a) to produce its corresponding F(ab')$_2$ fragment, designated as ZCE-F(ab')$_2$.

Dr. Mach refers to this antibody as Mab 35 in his publications.

To a 4 ml aliquot of final dialyzed solution from the pepsin digestion above, which contained 10 mg/ml ZCE-F(ab')$_2$, was added 10 μl of 0.5M DTPA and the reaction mixture was allowed to incubate for 10 minutes at 37° C. Thereafter, 160 μl of 0.5M cysteine was added and the reaction mixture was incubated at 37° C. for a further 10 minutes. The reaction mixture was then applied to a 40 ml P-6 column (Biorad Laboratories, Richmond, Calif.) that was pre-equilibrated and eluted with citrate buffered saline (50 mM ammonium citrate, 100 mM NaCl, 1 mM DTPA, pH 6.3). A 11.3 ml protein fraction was collected, which based upon its absorbance at 280 nm ($A_{280}$) was 79 μM in the reduced protein. The sulfhydryl content of the protein fraction was determined to be 149 μM, using DTNB as described in Example 12(b). The ratio of sulfhydryl groups per ZCE-Fab' fragment was calculated to be 1.9:1. The resultant fragment is designated ZCE-Fab'SH.

(e) Conjugation of CHA-Fab'BMP to ZCE-Fab'SH

To the 79 μM solution of ZCE-Fab'SH from Example 13(d) above was added dropwisely an amount of the 33 μm solution of CHA-Fab'BMP sufficient to provide a 1:1 ratio of ZCE-Fab'SH to reactive maleimide. The reaction mixture was allowed to stand overnight at 4° C. Thereafter, any unreacted sulfhydryl was blocked by the addition of 16 mg of DTNB to the reaction mixture, thereby providing a concentration of approximately 1 mM DTNB.

The resultant bifunctional antibody-like compound, designated as CHA-BMP-ZCE, was purified from the reaction mixture by a variety of techniques including high pressure liquid chromatography (HPLC) using as matrices either Fast Flow S (Pharmacia) or TSK-GEL SP-TOYOPEARL ® 650s cation exchange resin (Tosoh Corp., Japan); and by gel filtration on a Sephadex ® G-150 column (Pharmacia, Piscataway, N.J.). Those of ordinary skill in the art are familiar with protein purification via the techniques of HPLC, and gel filtration.

EXAMPLE 14

Preparation of Trifunctional Antibody-Like Compounds

Select three different intact antibodies designated herein as $Ab_1$, $Ab_2$, and $Ab_3$, which have the desired specificities and avidities. The antibodies are individually digested with pepsin according to conventional procedure, such as described in Example 12(a) herein, yielding F(ab')$_2$ fragments designated as $F_1(ab')_2$, $F_2(ab')_2$, and $F_3(ab')_2$, respectively.

The F(ab')$_2$ fragments derived from each of the three antibodies are reduced with cysteine (or other similar reducing agent) to their respective Fab' fragments, i.e., $F_1ab'$, $F_2ab'$, and $F_3ab'$, using a conventional procedure, such as described in Example 12(b) herein.

The three reduced Fab' fragments are selectively coupled together to form a trifunctional antibody-like compound via two trifunctional coupling agents of the present invention, e.g., tris(2-maleoylglycylaminoethyl)amine ("TMG") from Example 8. Procedurally, $F_1ab'$-SH, which has been dissolved in an aqueous buffer, pH 5-8, preferably pH 5-7, is added to a 30-fold molar excess of TMG dissolved in DMF. The reaction mixture is incubated at room temperature for 10 minutes. Thereafter, the reaction mixture is applied to a P-6 column (Biorad Laboratories, Richmond, Calif.) that has been pre-equilibrated and which is eluted with citrate buffered saline (50 mM ammonium [or sodium] citrate, 100 mM NaCl, 1 mM DTPA, pH 6.3). The protein fraction from the P-6 column (Biorad Laboratories) contains the purified $F_1ab'$-TMG which contains at least one maleimide moiety capable of coupling to a second reduced Fab' fragment.

To accomplish a second coupling to the TMG, the protein fraction containing the purified $F_1ab'$TMG is added dropwise to the second reduced Fab' fragment, $F_2ab'$SH which is in the same citrate buffer as used to elute the P-6 column. The second coupling reaction is allowed to proceed for 3 hours at room temperature. Thereafter, the extra sulfhydryls on the $F_2ab'$SH moiety of the coupled product, $F_1ab'$-TMG-$F_2ab'$SH, are protected by a reversible protecting agent, such as DTNB (5,5'-dithio-bis-(2-nitrobenzoic acid). Protection is begun by adding sufficient DTNB to achieve a final concentration of approximately 1 mM in the citrate buffered saline (50 mM ammonium citrate, 100 mM NaCl, 1 mM DTPA, pH 6.3) that contains the $F_1ab'$-TMG-$F_2ab'$SH. Thereafter, the reaction mixture is incubated for 10 minutes at room temperature. The resulting protected intermediate, $F_1ab'$-TMG-$F_2ab'$-S-blocking agent, is purified by high pressure liquid chromatography (HPLC), using a matrix comprising either Fast Flow S (Pharmacia, Piscataway, N.J.) or TSK-GEL SP-TOYOPEARL ® 650s (Tosoh Corp., Japan); or by preparative gel filtration, such as on a column containing Sephadex ® G-150 brand superfine resin (Pharmacia, Piscataway, N.J.).

Once purified, the protected intermediate, is deblocked in borate buffered saline (50 mM sodium borate, 50 mM NaCl, pH 8.2) to which is added a molar excess of 1 mM cysteine, DTT (dithiothreitol), or a similar reducing agent. The deblocked and reduced bifunctional intermediate is further purified by applying the reaction mixture to a P-6 column (Biorad Laboratories) which has been pre-equilibrated with and which is eluted with the just described citrate buffered saline, pH 6.3. The reduced bifunctional intermediate, $F_1ab'$-TMG-$F_2ab'$-SH, is now ready for coupling to a third maleimide derivatized Fab' fragment.

The third Fab' fragment is derivatized by being added to a 30-fold molar excess of TMG (or other trivalent coupling agent of the present invention) as described for the first Fab'-like fragment mentioned in this example. The reaction mixture is incubated at room temperature for 10 minutes. Thereafter, the $F_3ab'$-TMG in the reaction mixture is purified by applying the reaction mixture to a P-6 column (Biorad Laboratories) that has been pre-equilibrated with and which is eluted with the described citrate buffered saline, pH 6.3.

Final coupling to produce the trivalent antibody-like compound of the present invention is accomplished by adding $F_3ab'$-TMG to a solution of the above described citrate buffered saline (pH 6.3) containing the $F_1'$-TMG-$F_2ab'$SH and then allowing the reaction to proceed for 3 hours at room temperature. Thereafter, the reaction is stopped, such as by the addition of the alkylating agent, N-ethylmaleimide, to the reaction mixture. Purification of the trivalent antibody-like compound ($F_1$ab'-TMG-$F_2$ab'-TMG-$F_3$ab') is accomplished by HPLC, or preparative gel filtration (e.g., Pharmacia's Sephadex ® brand G-150 superfine resin), which are techniques well known to those of ordinary skill in the art.

EXAMPLE 15

Preparation Of The Trifunctional Antibody-Like Compound: CHA-BMP-CYA-BMP-ZCE

Three different antibodies, which were designated as CHA, CYA and ZCE, were the source of the Fab' fragments that were coupled by two trivalent coupling agents to form the trifunctional antibody-like compound, CHA-BMP-CYA-BMP-ZCE. In this example, the monoclonal antibody designated as CHA had specificity for the chelate complex In-EDTA or In-chelated by derivatives of EDTA, such as EOTUBE.

The monoclonal antibody designated as "CYA" had specificity for the chelate complex "Y-DTPA" and the monoclonal antibody designated as "ZCE" had specificity for carcinoembryonic antigen ("CEA").

(a) Preparation of F(ab')$_2$ Fragments

The F(ab')$_2$ fragments of CHA, CYA, and ZCE, which are designated as CHA-F(ab')$_2$, CYA-F(ab')$_2$, and ZCE-F(ab')$_2$ respectively, were prepared by individually digesting the respective antibody with pepsin according to the procedure described in Example 12(a).

(b) Reduction of CYA-F(ab')$_2$ to CYA-Fab'SH

To 1.0 ml of borate buffered saline (50 mM sodium borate, 50 mM NaCl, pH 8.2) containing 8.1 mg/ml of CYA-F(ab')$_2$, was added 2 μl of 0.5M diethylenetriaminepentaacetic acid (DTPA) and 40 μl of 0.5M cysteine. The reaction mixture was allowed to proceed for 10 minutes at 37° C. Thereafter, the reaction mixture was applied to a 15 ml P-6 column (Biorad Laboratories, Richmond, Calif. 94804) that had been pre-equilibrated and eluted with citrate buffered saline (50 mM ammonium citrate, 100 mM NaCl, 1 mM DTPA, pH 6.3). A 3.0 ml protein containing fraction was collected from the column, which based upon its absorbance at 280 nm ($A_{280}$) had a protein (reduced Fab') concentration of 48 μM. The concentration of free sulfhydryl groups in the protein fraction was determined to be 118 μM, using the procedure in Example 12(b) herein. Thereafter, the ratio of free sulfhydryl groups per Fab' fragment was calculated to be 2.5:1.

(c) Preparation of CHA-BMP-ZCE-SH

The bifunctional antibody-like compound, CHA-BMP-ZCE, having a blocked sulfhydryl, was prepared according to the procedure of Examples 13(a)–(e). Thereafter, to a 2.5 ml aliquot containing 3.9 mg/ml of the purified blocked CHA-BMP-ZCE in borate buffered saline (50 mM sodium borate, 50 mM NaCl, pH 8.2) was added 5 μl of 0.5M diethylenetriaminepentaacetic acid ("DTPA"). The reaction mixture was incubated for 15 minutes at 37° C. followed by the subsequent addition of 100 μl of 0.5M cysteine. The reaction mixture was further incubated for 10 minutes at 37° C., which effected deblocking. Thereafter, the reaction mixture was applied to a Biogel P-6 column (Biorad Laboratories) that had been pre-equilibrated and which was eluted with citrate buffered saline (50 mM ammonium citrate, 100 mM NaCl, 1 mM DTPA, pH 6.3). A 5.8 ml protein fraction was collected, which based upon its absorbance at 280 nm ($A_{280}$), had a 15 μM protein (reduced bifunctional antibody) concentration. The sulfhydryl concentration of the protein fraction was subsequently determined, according to the procedure in Example 10(a).

(d) Coupling CYA-BMP with CHA-BMP-ZCE-SH to form CHA-BMP-ZCE-BMP-CYA

To 5.5 ml of the citrate buffered saline solution that was 15 μM in CHA-BMP-ZCE-SH (from step (c) above) was added an equimolar amount of CYA-BMP similarly dissolved in citrate buffered saline (50 mM sodium citrate, 100 mM NaCl, pH 6.3). The reaction was allowed to proceed for 3 hours at room temperature and then was terminated by the addition of N-ethylmaleimide as described in Example 14 herein. The resultant trifunctional antibody-like compound, designated as CHA-BMP-ZCE-BMP-CYA, was purified by gel filtration on Sephadex ® G-150 (Pharmacia, Piscatway, N.J.), eluting with borate buffered saline (50 mM sodium borate, 50 mM NaCl, pH 8.2). Fractions 38–43 were collected and pooled to yield 3.2 ml of a solution containing 0.66 mg/ml of the purified product. A 2.0 ml aliquot of the pooled fractions was then dialyzed overnight in 0.17M sodium acetate, pH 4.5, for subsequent HPLC purification on a Mono S matrix (Pharmacia).

The uncorrected binding capacity for the In-EOTUBE complex by the CHA-BMP-ZCE-BMP-CYA in the 0.66 mg/ml pooled fraction was determined to be 76% of theoretical capacity. The control for the same run exhibited a binding capacity of 4%. The Y-MeTUBD binding capability was 82% of its theoretical value.

EXAMPLE 16

Synthesis Of The Trivalent Antibody-Like Compound: xCEM-TMG-xCHA-TMG-xCEM (a) Digestion of "xCHA" and "xCEM" to xCEM-F(ab')$_2$ and xCEM-F(ab')$_2$ Respectively.

Intact chimeric monoclonal antibody to the In-EDTA complex is designated herein as "xCHA." Intact chimeric monoclonal antibody to CEA is designated herein as "xCEM." The preparation of these antibodies was as referenced in Examples 11 and 12 herein. Intact xCHA and xCEM antibodies were individually digested to their respective F(ab')$_2$ fragments by incubating each with 3% (pepsin:antibody) at 37° C. for 5 hours in acetate buffered saline (100 mM sodium acetate, 100 mM sodium chloride, pH 4.1). The digests were terminated by neutralization of the pH. Thereafter the digests were dialyzed in borate buffered saline (50 mM sodium borate, 100 mM sodium chloride, pH 8.2) to provide the corresponding F(ab')$_2$ fragments designated as xCHA-F(ab')$_2$ and xCEM-F(ab')$_2$ respectively.

(b) Reduction of xCEM-F(ab')$_2$ to xCEM-Fab'SH

To 6 ml of xCEM-F(ab')$_2$ (17 mg/ml) obtained from Step (a) above was added 2.0 ml of borate buffered saline (50 mM sodium borate, 100 mM sodium chloride, pH 8.2) and 16 μl of 0.5M diethylenetriaminepentaacetic acid ("DTPA") to reach a final DTPA concentration of 1 mM. The reaction mixture was incubated at 37° C. for 10 minutes, followed by the addition of 360 μl of 0.5M cysteine, and a further incubation for 10 minutes at 37° C. The cysteine was removed by gel filtration on a 2.5×19 cm P-6 DG column (Biorad Laboratories, Richmond, Calif. 94804) that had been pre-equilibrated with and which was eluted with citrate buffered saline (50 mM ammonium citrate, 100 mM NaCl, 1 mM DTPA, pH 6.3). Upon elution, a 19.6 ml protein fraction was collected, which based upon its absorbance at 280 nm ($A_{280}$) was 90 μM in the reduced Fab' fragment-xCEM-Fab'SH. The free sulfhydryl concentration of the protein fraction was determined by reaction with DTNB (as per Example 10(a)) to be 159 μM. The ratio of free sulfhydryl per reduced Fab' fragment was calculated to be 1.8:1.

(c) Derivatization of xCEM-Fab'SH with TMG

The reduced Fab' fragment, xCEM-Fab'SH, was derivatized with a 30 fold molar excess of tris[2-N-(maleoylglycyl)aminoethyl]amine ("TMG"). In particular, 19.5 ml of xCEM-Fab'SH (1.8 μmoles) in citrate buffered saline from step (b) above was added with stirring to 176 μl of 314 mM TMG (53 μmoles) in DMF. After 10 minutes at 23° C., excess TMG was removed on a 2.5×45 cm P-6 DG column (Biorad Laboratories) that was pre-equilibrated and eluted with citrate buffered saline (50 mM ammonium citrate, 100 mM NaCl, 1 mM DTPA, pH 6.3). A 26.8 ml protein fraction was collected, which based upon its absorbance at 280 nm ($A_{280}$) contained 3.3 mg/ml or was 67 μM in the derivatized fragment-xCEM-Fab'-TMG. The determination of active maleimides by cysteine back titration (per Example 12(e)) indicated 1.16 active maleimides per Fab' fragment.

(d) Reduction of xCHA-F(ab')$_2$ To xCHA-Fab'SH

A 2.7 ml aliquot of xCHA-F(ab')$_2$ (9.2 mg/ml) was incubated with 1 mM DTPA for 10 minutes at 37° C. To this reaction mixture was then added 6 μl of 0.5M dithiothreitol ("DTT") and the reaction mixture was further incubated at 37° C. for a further 10 minutes. The DTT was removed by gel filtration on a 1.5×25 cm P-6 DG column (Biorad Laboratories) that was pre-equilibrated and eluted with citrate buffered saline (50 mM ammonium citrate, 100 mM NaCl, 1 mM DTPA, pH 6.3). A 7.6 ml protein fraction was collected, which based upon its absorbance at 280 nm ($A_{280}$) was 59 μM in the desired xCHA-Fab'SH. The free sulfhydryl concentration of the fraction was determined to be 236 μM. The ratio of free sulfhydryl groups per reduced Fab' fragment was calculated to be 4.7:1.

(e) Coupling xCHA-Fab'SH and xCEM-Fab'TMG

To 7.5 ml of xCHA-Fab'SH from step (d) above was added 26.2 ml of xCEM-Fab'-TMG from Step 15(c) above and the reaction mixture was incubated at 23° C. for 100 minutes. The reaction was terminated by the addition of 34 μl of 1M N-ethylmaleimide, an alkylating agent. The reaction mixture was then concentrated to 12 ml by ultrafiltration. The concentrated reaction mixture was purified by gel filtration on a 2.6×96 cm G-150 superfine column (Pharmacia, Piscataway, N.J.), having a bed volume of 500 ml. The flow rate was approximately 0.2 ml/min. and 5 ml fractions were collected. The $A_{280}$ trace of the elution pattern indicated 3 major products. The desired trivalent antibody-like compound, designated herein as xCEM-TMG-xCHA-TMG-xCEM, was found as the middle product, i.e., in fractions 38-41. The identity of the xCEM-TMG-xCHA-TMG-xCEM was confirmed by high pressure liquid chromatography (HPLC) gel filtration and by sodium dodecyl sulfate-polyacrylamide gel electrophoresis (SDS-PAGE) using a 7.5% acrylamide gel.

What is claimed is:

1. A method for extending the length of one of the three linker arms of the compound of Formula I defined as follows:

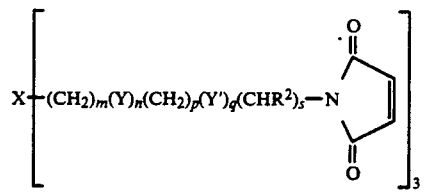

wherein X is

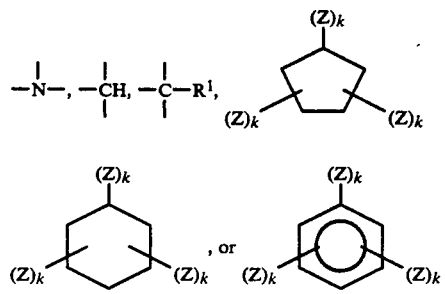

wherein k=1 or 0.
wherein Z is

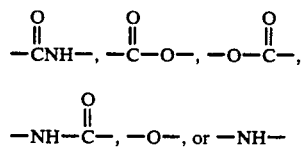

wherein s=1 or 0.
wherein n=1 or 0.
wherein q=1 or 0.
wherein Y is

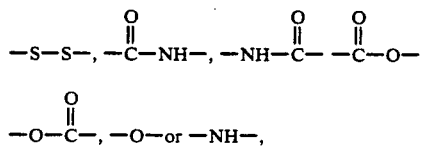

wherein Y', is

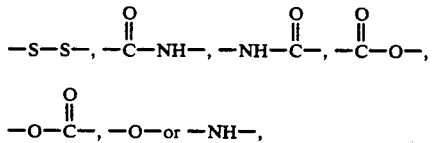

wherein p or m may be the same or different and are integers ranging from 0 to 20 with the proviso that when n=0, the sum of m and p is an integer ranging from 1 to 20, whereas when n=1, p and m are each an integer that is at least 1 and the sum of p and m is an integer ranging from 2 to 20.

wherein R$^1$ is straight or branched chain lower alkyl having from 1 to 6 carbon atoms or lower alkoxy having from 1-6 carbon atoms; and wherein R$^2$ is hydrogen, phenyl, —COOH, or straight or branched chain lower alkyl having from 1-6 carbon atoms, with the proviso that the lower alkyl moiety may be mono substituted by —NH$_2$, —OH, or —COOH
which method comprises:
(a) combining the compound of Formula I at pH 5-8 with an Fab' fragment having at least 2 free sulfhydryl groups to form a maleimide-Fab' complex having a single reactive maleimide extending distally therefrom;
(b) combining the maleimide-Fab' complex from step (a) at pH 5-8 with a compound of the formula:

$$HS-(CH_2)_t-SH \qquad II$$

wherein the subscript "t" is an integer from 2 to about 20, said compound of Formula II being combined in an amount effective to prevent intermolecular crosslinking between molecules of said Fab'-maleimide complex, said combination forming a coupled product between said maleimide-Fab' complex and said compound of Formula II, said coupled product having an extended linker arm with an —SH moiety extending distally therefrom;
(c) combining the coupled product of Step (b) at pH 5-8 with an amount of a bis-maleimide effective to prevent intermolecular crosslinking between molecules of said coupled product to form a maleimide-Fab' complex having an extended linker arm with a reactive maleimide at its terminus.

2. The method of claim 1 wherein the pH in Step (a) is 5-7.

3. The method of claim 2 wherein the pH in Steps (a) and (b) is 5-7.

4. The method of claim 3 wherein the bis-maleimide is a member selected from the group consisting of bis-(maleimido)-methyl ether; N'-bis(maleimidopropionyl)-2-hydroxyl-1,3-N,N'-o-phenylenedimaleimide; N,N'-p-propanediaminephenylenedimaleimide; and N,N'-(oxydimethylene)dimaleimide.

5. The method of claim 3 wherein the Fab' fragment is derived from an antibody that is a member selected from the group consisting of human IgG, primate IgG, mouse IgG$_1$, mouse IgG$_{2a}$, and mouse IgG$_{2b}$.

6. The method of claim 1 wherein the pH in Step (b) is 5-7.

7. The method of claim 1 wherein the Fab' fragment is derived from an antibody that is a member selected from the group consisting of human IgG, primate IgG, mouse IgG$_1$, mouse IgG$_{2a}$ and mouse IgG$_{2b}$.

8. The method of claim 1 wherein in Step (b), the compound of Formula II is combined in at least a 10 fold molar excess relative to said maleimide-Fab' complex.

9. The method of claim 8 wherein in Step (c) the bis-maleimide is combined in at least a 10 fold molar excess relative to the coupled product of Step (b).

* * * * *